United States Patent
Voigt et al.

(10) Patent No.: US 12,171,499 B2
(45) Date of Patent: Dec. 24, 2024

(54) EYE SURGERY SURGICAL SYSTEM HAVING AN OCT DEVICE AND COMPUTER PROGRAM AND COMPUTER-IMPLEMENTED METHOD FOR CONTINUOUSLY ASCERTAINING A RELATIVE POSITION OF A SURGERY OBJECT

(71) Applicant: Carl Zeiss Meditec AG, Jena (DE)

(72) Inventors: Christian Voigt, Abtsgmuend (DE); Stefan Saur, Aalen (DE); Christoph Hauger, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 837 days.

(21) Appl. No.: 17/161,536

(22) Filed: Jan. 28, 2021

(65) Prior Publication Data
US 2021/0228284 A1 Jul. 29, 2021

(30) Foreign Application Priority Data
Jan. 28, 2020 (DE) ...................... 10 2020 102 011.2

(51) Int. Cl.
*G06T 7/00* (2017.01)
*A61B 34/20* (2016.01)
(Continued)

(52) U.S. Cl.
CPC .............. *A61B 34/20* (2016.02); *A61F 9/007* (2013.01); *G06T 7/0012* (2013.01); *G06T 7/30* (2017.01);
(Continued)

(58) Field of Classification Search
CPC ......... A61B 34/20; G16H 30/40; A61F 9/007; G06T 7/0012; G06T 11/003
See application file for complete search history.

(56) References Cited

U.S. PATENT DOCUMENTS

2001/0007919 A1  7/2001  Shahidi
2017/0209042 A1*  7/2017  Matz ...................... A61B 3/102
(Continued)

FOREIGN PATENT DOCUMENTS

WO  2016/055422 A1  4/2016

OTHER PUBLICATIONS

Ehnes, A., "Entwicklung eines Schichtsegmentierungsalgorithmus zur automatischen Analyse von individuellen Netzhautschichten in optischen Kohärenztomographie—B-Scans", Dissertation, University of Giessen, chapter 3, pp. 45 to 82 (2013).
(Continued)

*Primary Examiner* — Edward Park
(74) *Attorney, Agent, or Firm* — Walter Ottesen, P.A.

(57) ABSTRACT

An eye surgery surgical system includes a device for displaying a relative position of a section of a surgery object in a 3D reconstruction of a region of an eye, a device for continuously providing at least two data records relating to at least partly overlapping portions of the region of the eye and of the section of the surgery object to a computer, a computer program for continuously ascertaining the relative position of the section of the surgery object and continuously ascertaining the 3D reconstruction of the eye from the data records provided. The program includes a first routine for continuously ascertaining the relative position of the section of the surgery object and the 3D reconstruction of the region of the eye from the data records provided via a registration method and a second routine for adapting the registration method based on a criterion.

20 Claims, 8 Drawing Sheets

(51) Int. Cl.
*A61F 9/007* (2006.01)
*G06T 7/30* (2017.01)
*G06T 7/70* (2017.01)
*G06T 11/00* (2006.01)
*G16H 10/60* (2018.01)
*G16H 30/40* (2018.01)
*A61B 3/10* (2006.01)
*A61B 34/10* (2016.01)
*A61B 90/00* (2016.01)

(52) U.S. Cl.
CPC .............. *G06T 7/70* (2017.01); *G06T 11/003* (2013.01); *G16H 10/60* (2018.01); *G16H 30/40* (2018.01); *A61B 3/102* (2013.01); *A61B 2034/105* (2016.02); *A61B 2034/107* (2016.02); *A61B 2034/2065* (2016.02); *A61B 2090/364* (2016.02); *A61B 2090/3735* (2016.02); *G06T 2207/10101* (2013.01); *G06T 2207/30041* (2013.01); *G06T 2207/30204* (2013.01)

(56) References Cited

U.S. PATENT DOCUMENTS

2018/0168737 A1* 6/2018 Ren .................... A61B 90/36
2019/0000563 A1* 1/2019 Schneider ............ A61B 34/20

OTHER PUBLICATIONS

Oliveira, F. et al.,"Medical Image Registration: a Review", Computer Methods in Biomechanics and Biomedical Engineering, Jan. 2014, https://www.researchgate.net/publication/221902046, 50 pages.
English translation and Office action of the German Patent Office dated Dec. 2, 2020 in German patent application 10 2020 102 011.2 on which the claim of priority is based.

\* cited by examiner

EYE SURGERY SURGICAL SYSTEM HAVING AN OCT DEVICE AND COMPUTER PROGRAM AND COMPUTER-IMPLEMENTED METHOD FOR CONTINUOUSLY ASCERTAINING A RELATIVE POSITION OF A SURGERY OBJECT

CROSS REFERENCE TO RELATED APPLICATION

This application claims priority of German patent application no. 10 2020 102 011.2, filed Jan. 28, 2020, the entire content of which is incorporated herein by reference.

FIELD OF THE INVENTION

The disclosure relates to an eye surgery surgical system including a visualization device for displaying a relative position of a section of a surgery object in a 3D reconstruction of a region of a patient's eye, including a device for continuously providing at least two data records relating to overlap regions in the form of at least partly overlapping portions of the region of the patient's eye and of the section of the surgery object to a computer unit, and including a computer program loaded in a program memory of the computer unit for continuously ascertaining the relative position of the section of the surgery object and continuously ascertaining the 3D reconstruction of the patient's eye from the at least two data records provided, wherein the computer program contains a first program routine for continuously ascertaining the relative position of the section of the surgery object and the 3D reconstruction of the region of the patient's eye from the at least two data records provided via a registration method and has a second program routine for adapting the registration method on the basis of a criterion. The disclosure also relates to computer program and a computer-implemented method for continuously ascertaining a relative position of a section of a surgery object and a 3D reconstruction of a region of a patient's eye.

The disclosure understands a surgery object to be both an object that can be used for an intervention in an operating region, that is, for example a surgical instrument, a section of a surgical instrument, in particular a tip of a vitreoretinal surgical instrument, a surgery robot or a section of a surgery robot, and a manipulator for a surgical instrument or a section of a manipulator for a surgical instrument and, in particular, an implant for a patient.

In the present case, the term a 3D reconstruction denotes the process of capturing the shape and the appearance of real objects or parts thereof. By way of example, the 3D reconstruction can be available as a depth map, a point cloud or a mesh. The process can be carried out using active or passive techniques. Active techniques actively interact with the object to be reconstructed in mechanical or radiometric fashion using distance measuring devices. By contrast, passive techniques only use a sensor in order to measure the radiation reflected or emitted by the surface of the object and use this to deduce the 3D structure of the object from an understanding of the image.

BACKGROUND OF THE INVENTION

Such an eye surgery surgical system and such a computer program are known from US 2018/0168737 A1. An ophthalmological imaging system is described therein, which combines, for example, OCT data and data from an optical microscope of a patient's eye and a surgery object positioned therein via a registration method. In the process, the position of the tip of the surgery object is captured and a priority region for the registration method is defined on the basis of the position of the tip, the registration method then being carried out in the priority region. When a position of the tip changes, the priority region is adapted accordingly.

US 2019/0000563 A1 describes a system for determining a relative position and orientation of an instrument tip during ophthalmological surgery. In this case, the tissue of the eye is captured via OCT, in particular, and the relative position and orientation of the instrument tip is determined via image capture, via magnetic sensors, via ultrasound sensors or via inertial sensors in a coordinate system referenced to the captured tissue on the basis of a marker attached to the instrument.

WO 2016/055422 A1 has disclosed an eye surgery surgical system including an OCT device and including a surgical instrument, which has an effective section that is localizable via the OCT device. WO 2016/055422 A1 specifies a tracking mode of operation for continuously ascertaining the spatial position of a surgical object embodied as an effective section of the surgical instrument in an object region volume of an object region.

US 2001/0007919 A1 has disclosed a navigation system for volume images, including a tracking system for ascertaining the relative position of a surgical instrument in three-dimensional perspective images of the operating region.

As a matter of principle, conventional eye surgery surgical systems facilitate a continuous determination of the relative position of a surgery object only in a spatially tightly delimited region of a patient's eye.

SUMMARY OF THE INVENTION

It is an object of the invention to enable a surgeon to precisely localize a surgery object in a patient's eye in a large region.

This object can, for example, be achieved by an eye surgery surgical system having: a visualization device for displaying a relative position of a section of a surgery object in a 3D reconstruction of a region of a patient's eye; at least one device for continuously providing at least two data records relating to overlap regions in a form of at least partly overlapping portions of the region of the patient's eye and of the section of the surgery object to a computer unit; a computer program for continuously ascertaining the relative position of the section of the surgery object and continuously ascertaining the 3D reconstruction of the patient's eye from the at least two data records provided, wherein the computer program is stored on a non-transitory computer readable medium of the computer unit; the computer program including a first program routine configured, when executed by a processor, to continuously ascertain the relative position of the section of the surgery object and the 3D reconstruction of the region of the patient's eye from the at least two data records provided via a registration method and including a second program routine configured to adapt the registration method on the basis of a criterion; and, wherein the criterion is at least one characteristic of the data records from measurement accuracy of the data records, number of data records, type of data records, and type or number of different modalities of the data records.

The object can, for example, also be achieved by an eye surgery surgical system having a visualization device for displaying a relative position of a section of a surgery object in a 3D reconstruction of a region of a patient's eye; at least one device for continuously providing at least two data records relating to overlap regions in a form of at least partly overlapping portions of the region of the patient's eye and of the section of the surgery object to a computer unit; a computer program for continuously ascertaining the relative position of the section of the surgery object and continuously ascertaining the 3D reconstruction of the patient's eye from the at least two data records provided, wherein the computer program is stored on a non-transitory computer readable medium of the computer unit; the computer program including a first program routine configured, when executed by a processor, to continuously ascertain the relative position of the section of the surgery object and the 3D reconstruction of the region of the patient's eye from the at least two data records provided via a registration method and including a second program routine configured to adapt the registration method on the basis of a criterion; and, wherein the criterion takes account of properties of at least one of the data records, the region of the patient's eye, the surgery object, the eye surgery surgical system, the registration method, a currently ascertained registration, and a type of surgery.

The object can, for example, also be achieved by an eye surgery surgical system having a visualization device for displaying a relative position of a section of a surgery object in a 3D reconstruction of a region of a patient's eye; at least one device for continuously providing at least two data records relating to overlap regions in a form of at least partly overlapping portions of the region of the patient's eye and of the section of the surgery object to a computer unit; a computer program for continuously ascertaining the relative position of the section of the surgery object and continuously ascertaining the 3D reconstruction of the patient's eye from the at least two data records provided, wherein the computer program is stored on a non-transitory computer readable medium of the computer unit; the computer program including a first program routine configured, when executed by a processor, to continuously ascertain the relative position of the section of the surgery object and the 3D reconstruction of the region of the patient's eye from the at least two data records provided via a registration method and including a second program routine configured to adapt the registration method on the basis of a criterion; and, wherein the criterion takes account of the availability of at least one of the data records, quality features of the region of the patient's eye in a form of a type or quality of tissue or material in the region, a size of the region, a type of surgery, quality features of the surgery object in a form of dimensions or material properties thereof, quality features of devices of the eye surgery surgical system in a form of settings of the eye surgery surgical system or properties of individual components or of an illumination setting, properties of the registration method in the form of its suitability for the data records present or the speed or accuracy thereof, and quality of a currently ascertained registration.

The object can, for example, also be achieved by a computer program for continuously ascertaining a relative position of a section of a surgery object and continuously ascertaining a 3D reconstruction of a region of a patient's eye from at least two data records provided, which relate to overlap regions in the form of at least partly overlapping portions of the region of the patient's eye and of the section of the surgery object. The computer program includes: program code stored on a non-transitory computer readable medium, said program code being configured, when executed by a processor, to ascertain the relative position of the section of the surgery object and of the 3D reconstruction of the region of the patient's eye is ascertained via a registration method which is adapted on the basis of a criterion; and, wherein the criterion takes account of at least one of properties of the data records, the region of the patient's eye, the surgery object, the eye surgery surgical system, the registration method, a currently ascertained registration, and a type of surgery.

The object can, for example, further be achieved via a computer program for continuously ascertaining a relative position of a section of a surgery object and continuously ascertaining a 3D reconstruction of a region of a patient's eye from at least two data records provided, which relate to overlap regions in the form of at least partly overlapping portions of the region of the patient's eye and of the section of the surgery object. The computer program includes: program code stored on a non-transitory computer readable medium, wherein said program code is configured, when executed by a processor, to ascertain the relative position of the section of the surgery object and of the 3D reconstruction of the region of the patient's eye via a registration method which is adapted on the basis of a criterion; wherein the criterion takes account of at least one of an availability of the data records, quality features of the region of the patient's eye in a form of a type or quality of tissue or material in the region, a size of the region, a type of surgery, quality features of the surgery object in a form of dimensions or material properties thereof, quality features of devices of the eye surgery surgical system in a form of settings of the eye surgery surgical system or properties of individual components or of an illumination setting, properties of the registration method in a form of its suitability for the data records present or the speed or accuracy thereof, and quality of the currently ascertained registration.

The object can, for example, also be achieved via a computer-implemented method for continuously ascertaining a relative position of a section of a surgery object and continuously ascertaining a 3D reconstruction of a region of a patient's eye from at least two data records provided, which relate to overlap regions in the form of at least partly overlapping portions of the region of the patient's eye and of the section of the surgery object, via a computer program stored on a non-transitory computer readable storage medium. The computer implemented method includes: ascertaining the relative position of the section of the surgery object and of the 3D reconstruction of the region of the patient's eye via a registration method which is adapted on the basis of a criterion; and, wherein the criterion is one of a first criterion, a second criterion and a third criterion; wherein the first criterion is at least one characteristic of the data records from measurement accuracy of the data records, number of data records, type of data records, and type or number of different modalities of the data records, wherein the second criterion takes account of at least one of properties of the data records, the region of the patient's eye, the surgery object, the eye surgery surgical system, the registration method, a currently ascertained registration, and a type of surgery; and, wherein the third criterion takes account of at least one of an availability of the data records, quality features of the region of the patient's eye in a form of a type or quality of tissue or material in the region, a size of the region, a type of surgery, quality features of the surgery object in a form of dimensions or material properties thereof, quality features of devices of the eye surgery surgical system in a form of settings of the eye surgery surgical system or properties of individual components or of an illumination setting, properties of the registration method in a form of its suitability for the data records present or the speed or accuracy thereof, and quality of the currently ascertained registration.

The eye surgery surgical system includes a visualization device for displaying a relative position of a section of a surgery object in a 3D reconstruction of a region of a patient's eye. It includes at least one device for continuously providing at least two data records relating to overlap regions in the form of at least partly overlapping portions of the region of the patient's eye and of the section of the surgery object to a computer unit. Here, a computer program is loaded in a program memory of the computer unit, the computer program being configured for continuously ascertaining the relative position of the section of the surgery object and continuously ascertaining the 3D reconstruction of the patient's eye from the at least two data records provided. Here, the computer program contains a first program routine for continuously ascertaining the relative position of the section of the surgery object and the 3D reconstruction of the region of the patient's eye from the at least two data records provided via a registration method and a second program routine for adapting the registration method on the basis of a criterion. Here, the criterion is at least one characteristic of the data records from the group of measurement accuracy of the data records, number of data records, type of data records, type or number of different modalities of the data records.

In the eye surgery surgical system, the criterion takes account of properties of the data records and/or of the region of the patient's eye and/or of the surgery object and/or of the eye surgery surgical system and/or of the registration method and/or of the currently ascertained registration and/or of the type of surgery.

In the eye surgery surgical system, the criterion takes account of the availability of the data records and/or quality features of the region of the patient's eye in the form of the type or quality of the tissue or material in the region and/or of the size of the region and/or of the type of surgery and/or quality features of the surgery object in the form of the dimensions or material properties thereof and/or quality features of devices of the eye surgery surgical system in the form of settings of the eye surgery surgical system or properties of individual components or of the illumination setting and/or of properties of the registration method in the form of its suitability for the data records present or the speed or accuracy thereof and/or the quality of the currently ascertained registration.

An eye surgery surgical system according to the disclosure allows a surgeon to navigate as accurately as possible in a large region of the patient's eye. By continuously ascertaining the 3D reconstruction and the relative position of the section of the surgical object in the 3D reconstruction, the data displayed to the surgeon via the visualization device are adapted to the real conditions. By way of example, movements of the patient are imaged directly by the continuous ascertainment of the 3D reconstruction. The continuous ascertainment of the relative position of the section of the surgery object and of the 3D reconstruction is advantageously implemented in real time in this case. Since the different portions of the region of the patient's eye are only captured by different modalities, the combination of the different data records by calculation via a registration method facilitates the ascertainment of a 3D reconstruction which represents a region of the patient's eye that is as large as possible.

The disclosure understands modalities to be different devices of the eye surgery surgical system, which devices serve to capture the structure, the appearance or measurement variables in the operating region. Modalities can be, for example, OCT devices, optical imaging devices, MRI apparatuses, CRT apparatuses, ultrasound apparatuses or sensors.

So that the registration method is able to combine the data records of different modalities by calculation, it is necessary for the at least two data records to image overlapping regions in the form of partly overlapping portions of the region of the patient's eye and of the section of the surgical object. Here, it is sufficient if each portion imaged by the data records present has an overlap region with one other portion imaged by the data records present. Moreover, it is advantageous if spatial relationships can be established between data records of different modalities by way of special features (including artificial features) or comparison data, for example, biometrically captured reference variables.

For registration methods, use can be made of methods known to a person skilled in the art, in particular methods for registering medical data, as are found in the publication "F. Oliveira, J. Tavares, Medical Image Registration: a Review, Computer Methods in Biomechanics and Biomedical Engineering, 2014", for example, the entirety of which is referenced herewith and the disclosure of which is incorporated herein in its entirety.

In an embodiment, the eye surgery surgical system includes a memory connected to the computer unit, for the purposes of providing data ascertained before surgery during surgery. These data ascertained before surgery originate from the group including images of the region of the patient's eye—for example, OCT images, ultrasonic images, MRI images, CT images or angiographies-images or data of a target area, distances, intended positions, geometric data of the surgical object, sensor signals, biometric patient data. This measure is advantageous in that additional data records recorded prior to surgery and further information items, for example, an intended position for surgical object or dimensions of surgical instruments, are available when ascertaining the 3D reconstruction and the relative position of the section of the surgical object. This facilitates a visualization of the operating region with increased accuracy.

Thus, it is possible to capture both the position of the portions of the anatomy of the patient's eye that are capturable from the outside, for example, portions of the head, of the sclera, of the iris, of the pupil or of the eyeball, and of the surgery object and possible further surgery objects, and also the position of portions of the patient's eye capturable from the inside, for example, the retina or certain tissues, or of the surgical object and possible further surgical objects within the patient's eye. Here, this capture of the regions of the patient's eye that are capturable from outside and from inside can be carried out via specific markers, marker-free topographic methods of 3D imaging, for example, OCT.

In particular, the simultaneous capture of portions of the region of the patient's eye and of the surgery object allows a relationship to be established between the portions captured within and outside of the patient's eye by way of additional information about the geometry and the dimensions of the surgical object.

These measures are advantageous in that the position of the surgery object and/or further surgery objects, for example, surgical instruments or implants, in the region of the patient's eye can be ascertained with the levels of accuracy that are as high as possible in relation to anatomical structures, target areas, intended positions or data ascertained before surgery, which are registered thereto. This reduces risks to the patient during surgery and only renders certain clinical pictures treatable.

In this case of posterior vitrectomy, this can avoid, for example, the vitrectome contacting the posterior capsular back and hence reduce the risk of a cataract. Within the scope of vitrectomy, knowledge of the distance between the tip and the retina is decisive in order to ensure a sparing removal of the vitreous humor there. When removing floaters, this measure facilitates targeted and precise detection and removal of the floaters with the vitrectome. In the case of implants for glaucoma surgery, knowledge of the position of the implant in the eye is decisive for the function of the implant and the obtainable reduction in pressure. In the case of membrane peeling on the retina, knowledge of the distance of the tip of the forceps from the retina is decisive for the safety during the treatment. The relative position and/or orientation within the capsular bag is of the essence in the case of toric intraocular lenses. In the case of so-called retinal vein cannulation, blocked vessels on the eye fundus must be treated. These are usually ascertained using angiographic methods, although these are not available during surgery or only available with a great outlay.

It is advantageous if the eye surgery surgical system is configured for the provision of the at least two data records relating to the overlap regions in the form of at least partly overlapping portions of the region of the patient's eye and of the section of the surgical object by at least one means from the group including data ascertained before surgery, images ascertained on the basis of an imaging method, sensor signals, biometric data. As a result of the use of various modalities and the combination with data ascertained before surgery and/or biometric data, a larger region of the patient's eye with a greater accuracy is ascertained by the eye surgery surgical system.

Advantageously, the at least one device for the continuous provision of at least two data records is configured to recognize at least one marker arranged at the surgery object and/or in a portion of the region of the patient's eye in order hence to localize the surgery object and/or the portion in the 3D reconstruction of the region of the patient's eye. Here, it is advantageous if this marker can be captured by the various modalities. Furthermore, it is advantageous if the at least one marker is uniquely assignable to the respective surgery object or region of the patient's eye. Moreover, it is advantageous if, for each marker, additional information items in respect of the surgery object or the region of the patient's eye, on which the marker is arranged, are stored in the eye surgery surgical system, the information items relating to the quality, structure, dimensions and/or appearance of the surgery object or region of the patient's eye. These measures firstly facilitate as accurate as possible localization of surgery objects provided with corresponding markers or a portion of the region of the patient's eye in an operating region. Secondly, the unique recognition and assignment of a marker to surgery objects or a portion of the region of the patient's eye in the operating region facilitates a more accurate registration of the data records of different modalities by virtue of corresponding markers being made to overlay via the registration method. Finally, the knowledge of the assignment between markers and surgical object or a portion of the region of the patient's eye in the operating region facilitates the use of additional knowledge about these regions during the registration of the data records. By way of example, if a marker belonging to an injection needle is localized in the data of a camera ascertained from the region of the patient's eye, information items about the dimensions of the injection needle can be used when ascertaining the 3D reconstruction of the region of the patient's eye and the relative position of the section of the surgical object. By way of example, if a camera only shows a section of a surgery object in the form of an injection needle which is situated outside of the patient's eye, knowledge of the dimensions of the section of the injection needle captured via the camera allows conclusions to be drawn from the visible part of the injection needle about the section of the injection needle, invisible to the camera, within the patient's eye. These information items can then again be combined by calculation with data records of different modalities, for example, OCT data, which capture the interior of the patient's eye. Thus, the attachment of markers is advantageous in that the visualization of the operating region can be carried out with greater accuracy.

To ascertain a 3D reconstruction with levels of accuracy that are as high as possible, the computer program is configured to adapt the registration method on the basis of a criterion. Here, it is advantageous if the computer program undertakes the adaptation of the registration method by virtue of altering the type of registration method and/or parameters of the registration method and/or the data records used by the registration method. As a result, it is possible to achieve a greater accuracy of the ascertained 3D reconstruction and relative position of the section of the surgery object since the registration method can be adapted directly to the currently available data records and/or circumstances during surgery. Moreover, this measure is advantageous in that, if data records of other regions of the patient's eye are available, these data records can be used as quickly as possible when ascertaining the 3D reconstruction and the relative position of the section of the surgery object, and so a greater region of the patient's eye can be visualized for the surgeon.

Moreover, it is advantageous if the registration method is continuously adapted during surgery. This ensures that the 3D reconstruction and relative position of the section of the surgery object, ascertained on the basis of the registration method, are adapted to the best possible extent during surgery to the requirements of the surgeon and the conditions during surgery. Moreover, this measure is advantageous in that, if data records of other regions of the patient's eye are available, these data records can be used as quickly as possible when ascertaining the 3D reconstruction and the relative position of the section of the surgery object. This measure ensures a greater accuracy and currentness of the visualized data.

Preferably, the criterion for adapting the registration method takes account of properties of the data records and/or of the region of the patient's eye and/or of the surgery object and/or of the eye surgery surgical system and/or of the registration method and/or of the currently ascertained registration and/or of the type of surgery. The criterion can be selected by the surgeon. Alternatively, it is also possible to store a list with priorities for the individual criteria in the eye surgery surgical system, which should be fulfilled to the best possible extent. On the basis of an optimization function, it is then possible to automatically select the registration method, the parameter set for the current registration method or the data records used in the registration method in such a way that they fulfill the priority list to the best possible extent for the given data and surgery conditions.

In particular, the criterion for adapting the registration method also takes account of the availability of the data records and/or quality features of the region of the patient's eye in the form of the type or quality of the tissue or material in the region and/or of the size of the region and/or of the type of surgery and/or quality features of the surgery object in the form of the dimensions or material properties thereof and/or quality features of devices of the eye surgery surgical system in the form of settings of the system or properties of individual components or of the illumination setting and/or of properties of the registration method in the form of its suitability for the data records present or the speed or accuracy thereof and/or the quality of the currently ascertained registration.

By selecting a suitable criterion, the surgeon can influence the properties of the ascertained 3D reconstruction and of the relative position of the surgery object. This provides them with greater flexibility when selecting a suitable visualization of the operating region. By way of example, they can select a registration method which has levels of accuracy that are as high as possible for the type of data records available. Alternatively, they might also select a registration method with a run time that is as short as possible. Alternatively, they might adapt the parameters of the registration method, for example the number of iterations when calculating the 3D reconstruction, in order to obtain a run time that is as short as possible or levels of accuracy that are as high as possible. In the case of significant reflection of the light at the tissue recorded, it is possible, for example, to use only in the registration method data records of modalities in which less strong or no reflections occur.

Specifications which, when selected, must be satisfied can also be stored in the eye surgery surgical system for the various registration methods, parameter sets or input data. By way of example, a maximum number of data records can be specified for a registration method. Should this number be exceeded, a different registration method is selected automatically. Alternatively, it is possible to store a list of modalities which can be processed by a registration method. Depending on the type of surgery, it is also possible to specify a list of suitable registration methods, parameters sets and/or input data records. Additional specifications such as quality information items and required calculation time are likewise helpful when the registration method or the parameters set is selected by the surgeon or when the routine for adapting the registration program is selected.

Preferably, the computer program contains a routine for determining a target area for the surgery object in the region of the patient's eye.

This disclosure understands a target area to be a portion in the 3D reconstruction of the object region volume, in which the surgery object should be brought to bear by virtue of a function of the surgery object being carried out or by virtue of the surgery object being placed there. To this end, this portion can obtain an intended position.

Furthermore, it is advantageous for the computer program to generate a guide variable for the surgery object in respect of this target area.

The disclosure understands a guide variable to be a variable which is ascertained by the computer program and which serves to guide a surgery object in the region of the patient's eye. Here, such a variable denotes a quantitatively determinable property of a procedure or state when guiding the surgical object. Here, the guide variable can directly describe the guiding of the surgery object, for example in the form of a direction, a speed, a position or a temporal extent. The guide variable can also describe the guiding of the surgery object indirectly, for example in the form of an amount, a volume or a spatial extent of a medium which should be discharged into or removed from the region of the patient's eye via the surgery object. Here, the guide variable is advantageously ascertained by processing data of the target area. By way of example, a guide variable can be control signals for the surgery object in the form of a surgical instrument, an amount of medium to be discharged into the region of the patient's eye at an intended position, for example, stem cells, or an amount of tissue to be removed, for example when removing vitreous humor.

Ascertaining the target area in the 3D reconstruction of the object region volume and determining the guide variable for the object by the computer program facilitate an automation of the guidance of surgery objects during a surgical operation.

Preferably, the computer generates an actuating signal for triggering a function of the surgery object and/or a device of the eye surgery surgical system on the basis of the relative position of the surgery object, for example, in the form of a surgery instrument or implant, in the 3D reconstruction of the region of the patient's eye and/or the type of surgery. The function can be a display or an activation of a suitable visualization. Parts of the surgery object, for example, the tip of the surgical instrument, can be augmented in the process. The function can also provide a deactivation of a surgery object, for example, a surgical instrument or micro robot, when a minimum distance is no longer maintained between the surgery object and a portion of the region of the patient's eye in order to avoid unwanted contact. The function can also control the adaptation of the power output of a surgery object, for example, a surgical instrument in the form of a phaco handpiece, when critical distances are reached. Moreover, the function can undertake path/force scaling on the basis of the distance of the surgical object from critical tissue. In the case of unwanted head and/or eye movements the function can bring about an automated retraction of the surgical object from the eye. As an alternative or in addition thereto, it is also possible for the function to compensate intra-surgical position changes of the site in order to maintain a relative position between the surgical object and the site. An automated adjustment of the remote center of motion to a surgical object, for example, a trocar, is also conceivable. The function can however also bring about an automated adaptation of a therapeutic apparatus; by way of example, this allows more regular patterns of the laser spots to be generated in the case of laser photocoagulation for the purposes of fastening the retina. If the surgical object, for example, in the form of injector, is in the correct relative position it is possible to automatically administer medicaments. Finally, the adaptation of the therapeutic apparatus can regulate the radiation power of an intra-surgical radiotherapy system for the purposes of sparing healthy tissue or for the locally differentiated distribution of the radiation distribution in the site.

The computer program preferably contains a routine for determining a target area and/or an intended position for the object in the data ascertained before surgery and a registration routine for registering the data ascertained before surgery with the 3D reconstruction of the region of the patient's eye and a transfer routine for transferring the target area and/or the intended position in the data ascertained before surgery to the 3D reconstruction of the region of the patient's eye. As a result, it is possible to automatically transfer information items such as target areas and/or intended positions from the data ascertained before surgery to the 3D reconstruction present. This facilitates comprehensive automation of the operating method and an accurate localization of the target area and/or the intended position in the 3D reconstruction on the basis of the pre-surgical data.

It is moreover advantageous if the computer program is configured to determine target areas and/or intended spatial positions in the data ascertained before surgery and/or in the 3D reconstruction of the region of the patient's eye by virtue of applying methods for segmenting tissue structures and/or tissue layers. This measure contributes to a higher degree of automation of the operating method.

An advantageous embodiment includes a device for visualizing the relative position of the section of the surgery object in the 3D reconstruction of the region of the patient's eye and/or of data ascertained before surgery and/or a guide variable to be determined in relation to a target area and/or variables derived from this guide variable. As a result, a surgeon can permanently monitor the relative position of the surgery objects, for example, the relative position of implants of surgical instruments, within the 3D reconstruction of the object region volume. Data ascertained before surgery can likewise be visualized in order to display to the surgeon, for example, the target area ascertained before surgery or further information items planned prior to surgery. Ascertained guided variables such as control signals for displacing the objects and amounts of a volume to be discharged or of a substance to be removed can also be visualized for the surgeon. This also applies to variables derived from a guide variable, for example a volume to be corrected, which is determined from a previously ascertained guide variable in the form of an intended value for the volume to be discharged. The computer program can generate acoustic, optical or haptic indication signals for the surgeon on the basis of the guide variable ascertained in relation to the target area and/or variables derived therefrom.

A further embodiment provides for the visualization device to augment data when displaying the relative position of the section of the surgical object in the 3D reconstruction of the region of the patient's eye, wherein the augmented data contain concealed regions in the 3D reconstruction and/or concealed regions of the surgery object and/or measurement values and/or distances and/or intended positions and/or geometric information items in respect to the surgical object.

Here, it is possible to augment, for example, occluded data such as concealed regions of the surgery object or diagnostic data located below the surgery object. It is also possible to augment a non-visible effective region of a surgical object, for example the capture region of an OCT probe or of an endoscope or the lateral exit of a cutter at a vitrectomy. As an alternative or in addition thereto, it is also possible to augment numerical values, for example, measured variables such as the distance between surgical object and retina, in the visualization of the region of the patient's eye. The numerical values can be indicated, for example, numerically or as a color scale or via acoustic or haptic signals. Finally, it is also advantageous to augment intended positions for a surgical object, for example, an intended position for attaching an implant or an intended position for discharging a medium in the region of the patient's eye, or deviations of the surgical object from this intended position.

The disclosure also extends to a computer program for continuously ascertaining a relative position of a section of a surgery object and continuously ascertaining a 3D reconstruction of a patient's eye from at least two data records provided, which relate to overlap regions in the form of at least partly overlapping portions of the region of the patient's eye and of the section of the surgery object, wherein the relative position of the section of the surgery object and of the 3D reconstruction of the region of the patient's eye is ascertained via a registration method which is adapted on the basis of a criterion.

Moreover, the disclosure extends to a computer-implemented method for continuously ascertaining a relative position of a section of a surgery object and continuously ascertaining a 3D reconstruction of a patient's eye from at least two data records provided, which relate to overlap regions in the form of at least partly overlapping portions of the region of the patient's eye and of the section of the surgery object, via an above-described computer program.

BRIEF DESCRIPTION OF THE DRAWINGS

The invention will now be described with reference to the drawings wherein.

DESCRIPTION OF THE PREFERRED
EMBODIMENTS OF THE INVENTION

Figure 1:
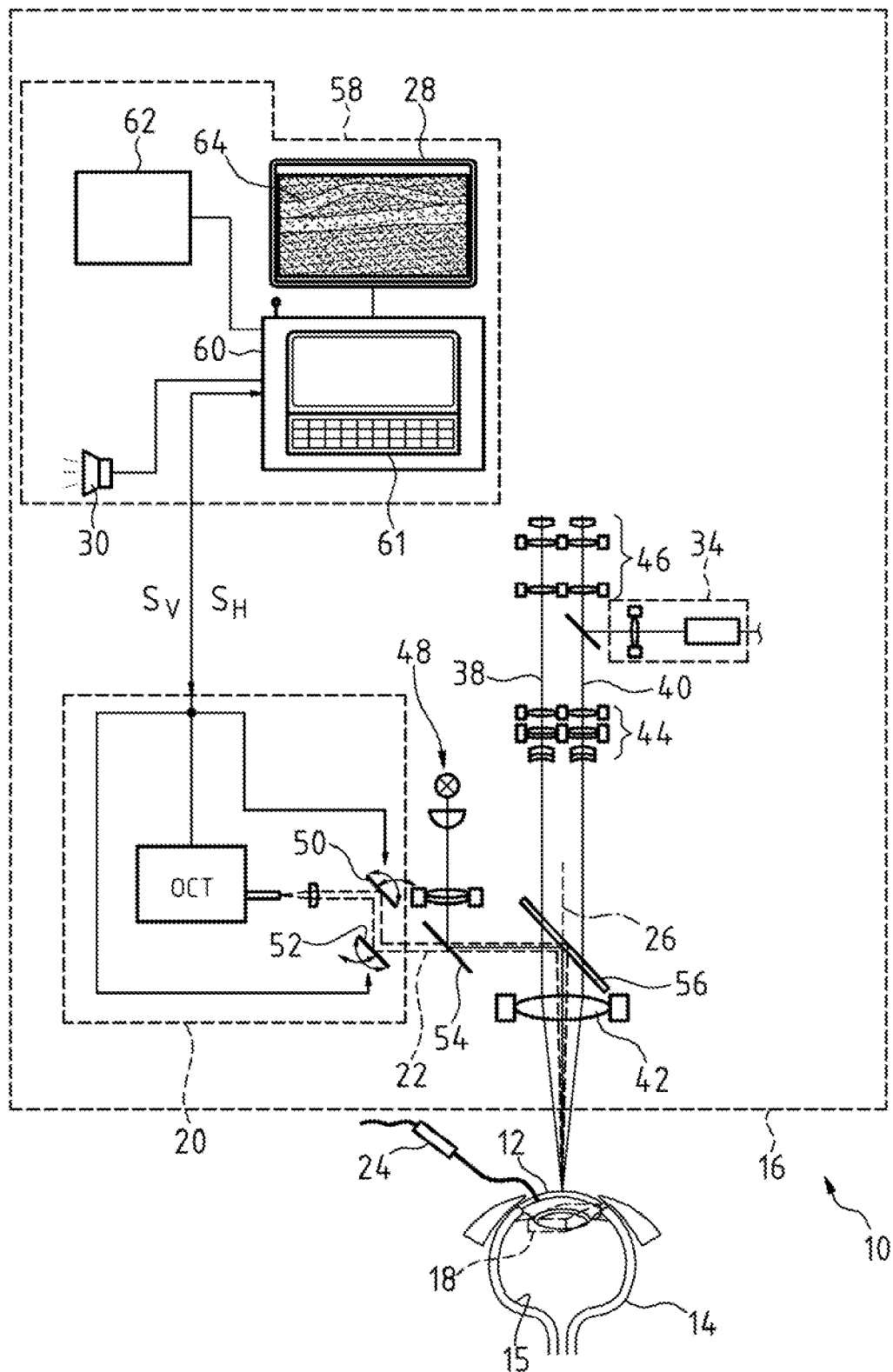
FIG. 1 shows a first eye surgery surgical system including a surgical microscope and an OCT device for scanning a region of a patient's eye with a surgery object in the form of a surgical instrument therein.

The first eye surgery surgical system 10 shown in FIG. 1 contains a surgical microscope 16 for visualizing a region 18 of a patient's eye 14 with magnification. By way of example, the surgical microscope 16 can be embodied as an OPMI® Lumera 660 Rescan surgical microscope by Carl Zeiss Meditec AG. The surgical microscope 16 includes a stereoscopic observation beam path 38, 40, which facilitates the examination of the patient's eye 14 through a microscope main objective 42 in the region 18 of the patient's eye 14. The surgical microscope 16 further includes a zoom system 44 and an eyepiece 46. It includes an illumination device 48 which illuminates region 18 of the patient's eye 14 with illumination light through the microscope main objective 42 for the purposes of stereoscopically visualizing the patient's eye 14 in the eyepiece 46.

The eye surgery surgical system 10 contains at least one surgery object 24, which has a section 84 that is arrangeable in the region 18 of the patient's eye 14. The surgery object 24 is an injection needle for injecting stem cells in the retina 15 of the patient's eye 14. Here, the injection needle is localizable on the basis of a marker 78.

The eye surgery surgical system 10 furthermore contains a device for continuously providing at least two data records relating to overlap regions in the form of at least partly overlapping portions of the region 18 of the patient's eye 14 and of the section 84 of the surgical object 24 to a computer unit 60. This device is embodied as an OCT device 20 which provides an OCT scanning beam 22 for scanning the region 18 of the patient's eye 14 with an A-, B- and C-scan, as described, for example, in chapter 3, pages 45 to 82 in A. Ehnes, "Entwicklung eines Schichtsegmentierungsalgorithmus zur automatischen Analyse von individuellen Netzhautschichten in optischen Kohärenztomographie—B-Scans", Dissertation, University of Giessen (2013).

Optical coherence tomography (OCT) is a method for capturing volume data, in particular of biological tissue, by scanning the tissue via an OCT scanning beam 22 made of temporally incoherent but spatially coherent laser light, which is guided in a sample beam path and a reference beam path. OCT allows the localization of objects such as, for example, surgical objects 24 in a region 18 of a patient's eye 14.

The OCT device 20 provides the OCT scanning beam 22 with short coherent light, which is guided through the microscope main objective 42 to the region 18 of the patient's eye 14 by way of adjustable scanning mirrors 50, 52 and beam splitters 54, 56. The light of the OCT scanning beam 22 scattered in the region 18 of the patient's eye 14 returns at least in part to the OCT device 20 via the same light path. Then, the light path of the scanning light is compared in the OCT device 20 to a reference path. Using this, it is possible to capture the precise position of scattering centers in the region 18 of the patient's eye 14, in particular the position of optically effective areas, with an accuracy which corresponds to the coherence length $I_c$ of the short coherent light in the OCT scanning beam 22.

In the surgical microscope 16, there is a device 58 for controlling the OCT scanning beam 22 and for setting the position of the region 18 of the patient's eye 14 scanned by the OCT scanning beam 22. The device 58 contains a computer unit 60. The computer unit 60 has an input interface 61 as a means for entering intended values and contains a computer program for controlling the OCT scanning beam 22 and adjusting the spatial extent and position, that is, the relative position and orientation, of the region 18 of the patient's eye 14 scanned by the OCT scanning beam 22. The device 58 for controlling the OCT scanning beam 22 is embodied in this case for successive continuous scanning of the region 18 of the patient's eye 14 and of the region 18 of the patient's eye 14 containing the section 84 of the object 24 via the OCT scanning beam 22. Here, the OCT scanning beam 22 has a frame rate of 10 ms to 20 ms in order to allow fast hand-eye coordination of the surgeon.

Further, the computer program in the program memory of the computer unit 60 contains a control routine which specifies the reference length for the OCT scanning beam 22 and the settings of the adjustable scanning mirrors 50, 52 for scanning the region 18 of the patient's eye 14. There is a control member 62, actuatable by an operator, in the device 58 for setting the region 18 scanned via the OCT scanning beam 22. The control routine moreover contains a scanning routine for scanning the region 18 of the patient's eye 14 and the section 84 of the surgery object 24 using specific scanning patterns. In the process, the region 18 of the patient's eye 14 is scanned at a lower rate than the section 84 of the surgery object 24 in order to keep the amounts of data as small as possible and hence the computation time as short as possible.

The computer program in the program memory of the computer unit 60 contains a first program routine for continuously ascertaining a 3D reconstruction 94 of the region 18 of the patient's eye 14 and for continuously ascertaining the relative position of the section 84 of the surgery object 24 in the region 18 of the patient's eye 14 by processing at least two data records via a registration method, wherein the at least two data records have been captured with the OCT device 20 by scanning at least partly overlapping portions of the region 18 of the patient's eye 14 and of the surgery object 24.

A second program routine in the computer program serves to adapt the registration method on the basis of a criterion. In the process, the input data of the registration method are adapted during surgery to the availability and measurement accuracy of the data provided in order to obtain greater accuracy. If the measurement accuracy of individual data points is too low, these are not taken into account by the registration method.

The device 58 for controlling the OCT scanning beam 22 contains a visualization device 28, connected to the computer unit 60, in the form of a display for displaying a relative position of a section 84 of the surgery object 24 in the 3D reconstruction 94 of the region 18 of the patient's eye 14 scanned by the OCT scanning beam 22 and a user interface. Moreover, in the eye surgery surgical system 10, the OCT scanning information item from the OCT device 20 may be visualized for a surgeon in the eyepiece 46 of the surgical microscope 16 via a device for mirroring-in data 34.

The computer program moreover contains a calculation routine for ascertaining a target area 90 in the 3D reconstruction 94 of the region 18 of the patient's eye 14. A guide variable for the surgery object 24 is determined in relation to the target area 90.

Here, in the present case, a guide variable is understood to be a variable which is ascertained by the computer program which serves to guide the surgery object 24 in the region 18 of the patient's eye 14. When placing a surgery object 24 in a target area 90 of the retina 15, a direction or speed, for example, for the placement of the surgical object 24 is specified as guide variable.

The computer unit 60 connected to the OCT device 20 generates additional indication signals 30. Within the scope of placing the surgery object 24 at the retina 15, an indication signal 30 in the form of an acoustic signal is generated when the intended position 91 is reached.

The ascertained guide variables can be processed by the control unit of a micro robot which controls the surgery object 24. The control of the surgery object 24 by the micro robot can be monitored and corrected by a surgeon. Alternatively, the surgeon can also directly carry out the control of the surgery object 24 themselves.

Figure 2:
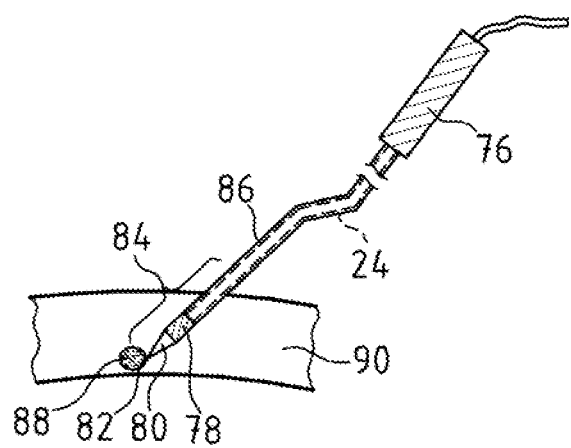
FIG. 2 shows a surgery object in the form of an injection needle.

FIG. 2 shows a surgery object 24 in the form of an injection needle. The injection needle has a section 84 which acts as an effective section and has a handle section 76 which can be held by the surgeon or, as an alternative thereto, by a micro robot, too. The injection needle contains a capillary 86 and has a tip 80 with an opening 82 for discharging a medium 88 in the target area 90. There is a marker 78 that is localizable via the OCT scanning beam 22 at the injection needle.

Figure 3:
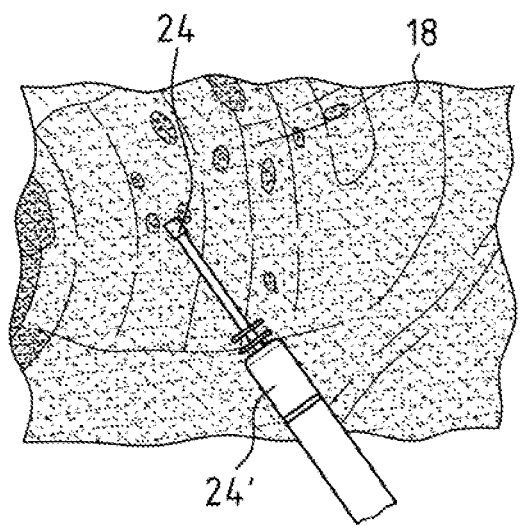
FIG. 3 shows a surgery object in the form of a retinal pin.

FIG. 3 shows a surgery object 24 in the form of a retinal pin, which serves to fasten a further surgery object 24' in the form of an implant to the retina 15.

Figure 4:
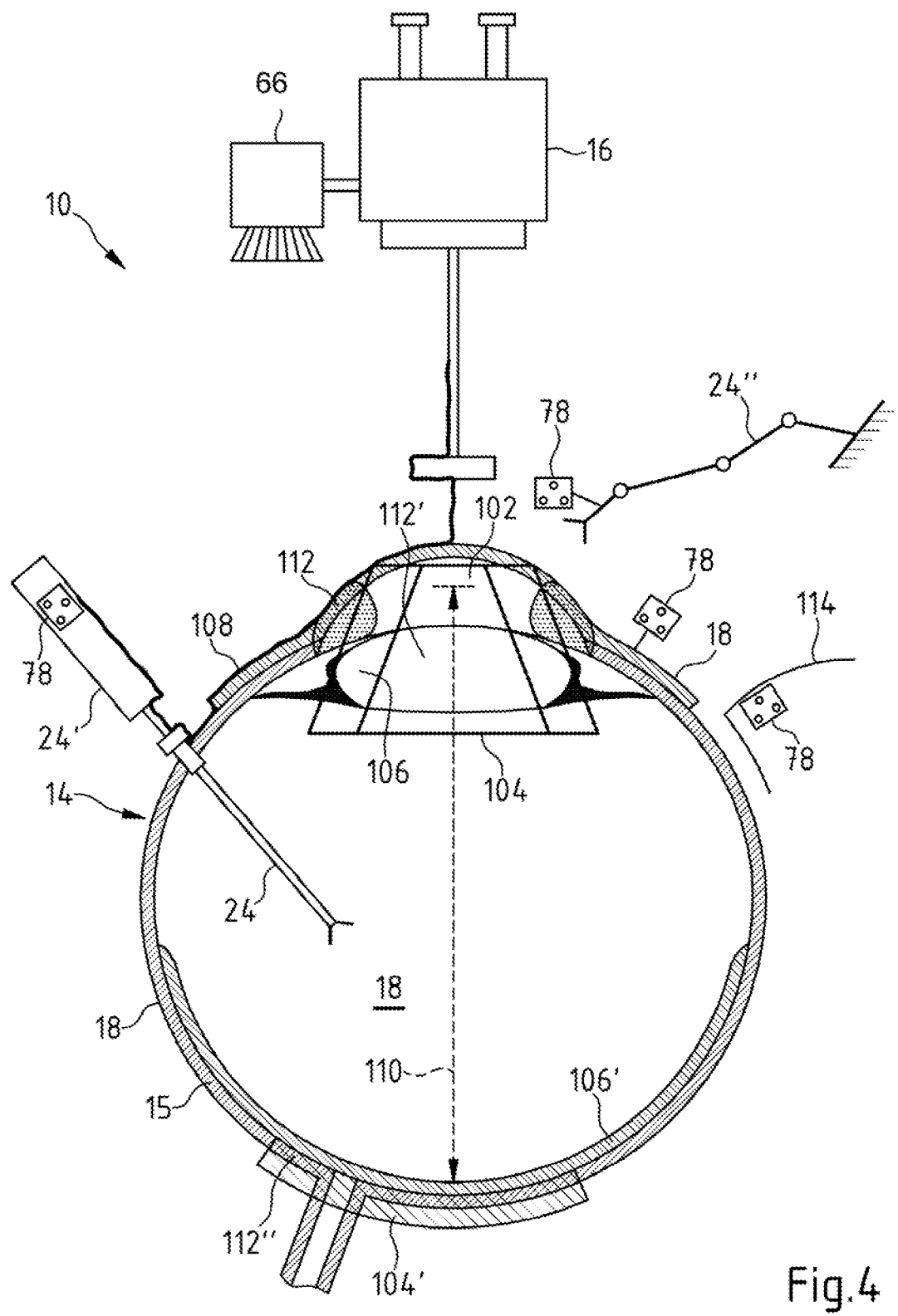
FIG. 4 shows an eye surgery surgical system including various modalities in the form of a surgical microscope, an OCT device and an image capturing device for capturing different, at least partly overlapping portions of a region of a patient's eye.

FIG. 4 shows a region 18 of a patient's eye 14 which is recorded by a plurality of modalities in the form of a surgical microscope 16, an image capturing device 66 and an OCT device 20. A surgery object 24 in the form of a surgical instrument embodied as a trocar is arranged in the patient's eye 14. With the aid of a trocar, access to a body cavity is created and kept open by a tube in the minimally invasive surgery. The trocar is placed in the patient's eye 14 with a further surgery object 24' in the form of an applicator. A micro robot is a further surgery object 24". Markers 78 serving localization purposes in the region 18 of the patient's eye 14 are attached to the surgical objects 24, 24', 24"—the trocar, the applicator and the micro robot—and in the region 18 of the patient's eye 14 and also at further points in the surroundings such as a head 114 of the patient. Here, the markers can be detected by all modalities, that is, by the OCT device, the image capturing device and the surgical microscope. Moreover, the individual markers are distinguishable from one another such that each modality can ascertain the marker in question. Different modalities capture different portions of the region 18 of the patient's eye 14. Thus, the OCT device 20 captures the front OCT capture region 104 in the vicinity of the pupil 102 of the patient and the back OCT capture region 104' on the retina 15. The surgical microscope 15 captures the front surgical microscope capture region 106 in the vicinity of the pupil 102 of the patient and the back surgical microscope capture region 106' on the retina 15. The image capturing device 66 in the form of a camera captures the camera capture region 108.

What should be noted here is that these different modalities each capture different portions within and outside of the patient's eye 14. The image capturing device 66 in the form of the camera captures the outer region of the patient's eye 14 and the surgery objects 24, 24'. The surgical microscope 16 and the OCT device 20 capture both outer regions of the patient's eye 14 and inner regions of the patient's eye 14, for example, parts of the retina 15. Here, each capture region 104, 104', 106, 106', 108 has, at least in part, an overlap region 112, 112', 112", 112''' with at least one further capture region 104, 104', 106, 106', 108. The camera capture region 108 and the front surgical microscope capture region 106 have the overlap region 112. The front OCT capture region 104 and the front surgical microscope capture region 106 have the overlap region 112'. The back OCT capture region 104' and the back surgical microscope capture region 106' have the overlap region 112" on the retina 15. These overlap regions 112, 112', 112" allow the spatial relationship to be established between the data captured by the individual modalities using the registration method and hence facilitate a 3D reconstruction 94 of the region 18 of the patient's eye 14, which reconstruction contains both inner regions of the patient's eye 14 and outer regions of the patient's eye 14. In particular, regions of surgery objects 24, 24', 24" within and outside of the patient's eye 14 can be observed by combining the data from different modalities.

Biometric patient data can also be used to create the 3D reconstruction 94 of the region 18 of the patient's eye 14, for example biometric patient data in the form of the eye length 110 identified in FIG. 4, that is, the distance between retina 15 and pupil. These data can be ascertained before surgery. However, they can additionally be included in the process of ascertaining the 3D reconstruction 94.

Furthermore, the features of the surgical objects 24, 24', 24", for example, dimensions, angles or distances, can also be used when creating the 3D reconstruction. By way of example, if the position of a portion of a surgery object 24, 24', 24" outside of the eye is known, the position of other regions of this surgery object 24, 24', 24" within the patient's eye can be deduced from the known dimensions of the surgery object 24, 24', 24".

Moreover, sensor signals, for example, distance signals, can be used when ascertaining the 3D reconstruction.

The combination of all these various data sources by the registration methods allows the simultaneous use of all captured data in every visualization of the region 18 of the patient's eye 14.

The computer program in the computer unit 60 ascertains the relative position of the section of the surgery object and the 3D reconstruction of the patient's eye continuously in a first program routine from the provided at least two data records via a registration method. A second program routine is configured to adapt the registration method on the basis of a criterion. This adaptation likewise occurs continuously during the operation. Here, the criterion considers the availability of the data records, the measurement accuracy thereof and the number thereof. If the data records of certain modalities are not available or are of low measurement accuracy, it is sensible not to use these in the registration method. To exclude these data records, the surgeon can set a threshold for the measurement accuracy, above which a data record is used for the registration method. This ensures that the ascertain ascertained 3D reconstruction 94 reliably represents the observed region 18 of the patient's eye 14 for the surgeon. The number of data records also has effects on the accuracy of the ascertained 3D reconstruction. The more data records of a portion of the region 18 of the patient's eye 14 are available, the more accurate the 3D reconstruction ascertained from the data records is. It is also possible to select the registration method itself depending on the type and/or number of data records. Registration methods that can only process data from one modality are not suitable for the ascertainment of a 3D reconstruction if much data of other modalities is available. Registration methods which exploit particular properties of one modality are not suitable for registering data of other modalities. Since the method should run in real time, it is expedient to change the registration method or its parameters if a large number of data records are available in order to be able to meet the real-time requirement. By contrast, if a low number of data records are available, it is expedient to use a more accurate registration method, which supplies a 3D reconstruction 94 of higher quality.

Data are augmented when the relative position of the section 84 of the surgery object 24, 24', 24" in the 3D reconstruction 94 of the region 18 of the patient's eye 14 is displayed by the visualization device 28. These data contain concealed regions of the 3D reconstruction 94 and/or concealed or non-captured regions of the surgery object 24 and/or measurement values and/or distances and/or intended positions 91 and/or geometric information items relating to the surgery object 24. By way of example, if the relative position of a surgery object 24, 24', 24" is only captured in regions outside of the patient's eye 14 by the data records, the relative position of the surgery object 24, 24', 24" within the patient's eye 14 can be deduced on the basis of the known dimensions of the surgery object 24, 24', 24" and these non-captured regions can be augmented and also displayed by the visualization device 28.

The computer program moreover generates an actuating signal for adapting the visualization of the 3D reconstruction 94 of the region 18 of the patient's eye 14 with the section 84 of the surgery object 24.

Figure 5:
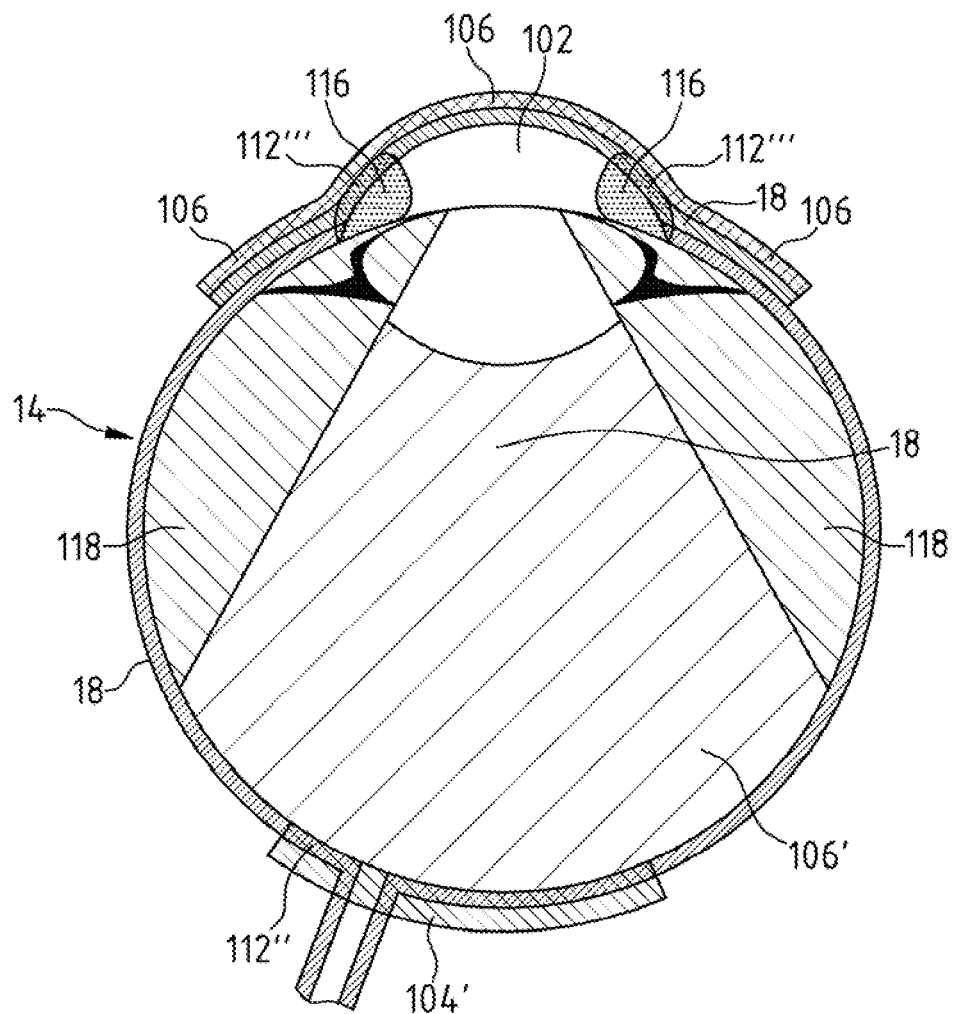
FIG. 5 shows capture regions of different modalities in the form of a surgical microscope, an OCT device and a gonioscope.

FIG. 5 shows capture regions 104', 106, 106', 116 of different modalities in the form of an OCT device 20, a surgical microscope 16 and a gonioscope in the region 18 of the patient's eye 14. The back OCT capture region 104' has an overlap region 112" with the back surgical microscope capture region 106'. The front surgical microscope capture region 106 has an overlap region 112" with the gonioscope capture region 116. The region 118 is not captured by any modality.

Figure 6:
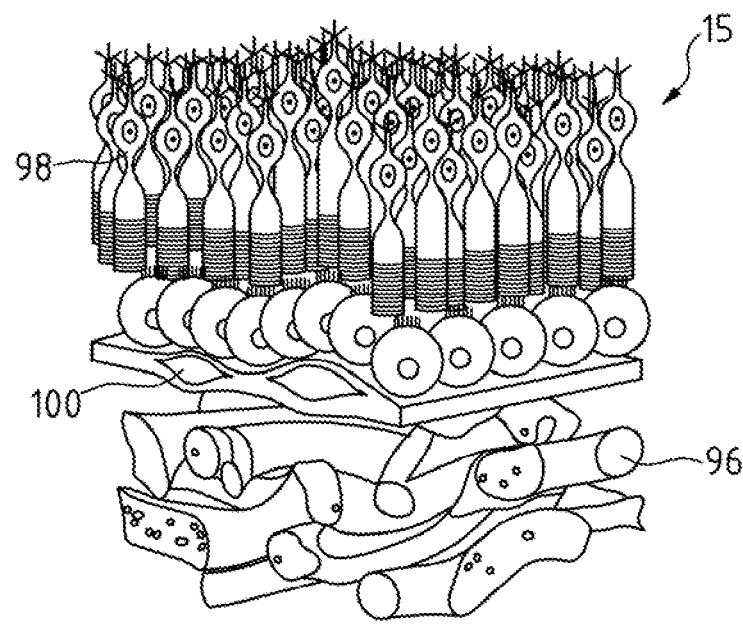
FIG. 6 shows a section of a portion of the retina.

FIG. 6 illustrates the structure of the retina 15 of the patient's eye 14, including blood vessels 96 as well as photoreceptors 98 and drusen 100.

Figure 7:
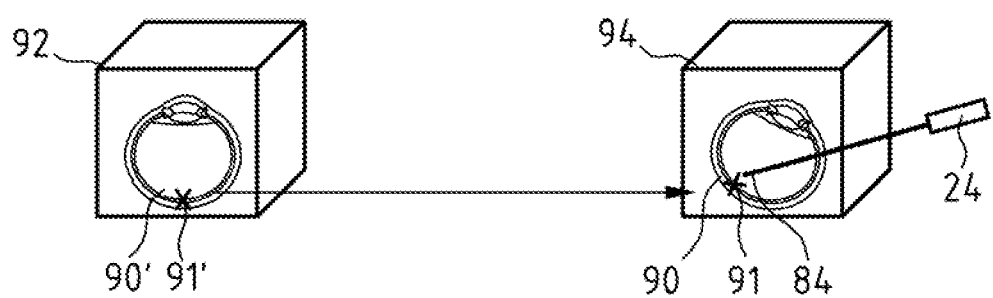
FIG. 7 shows a transfer of a target area based on pre-surgical data to a 3D reconstruction of a region of the patient's eye.

FIG. 7 shows a transfer of the target area 90' based on data 92 ascertained before surgery to a 3D reconstruction 94 of a region 18 of a patient's eye 14 in the computer unit 60. To ascertain a target area 90 in the 3D reconstruction 94 of the region 18 of the patient's eye 14, data 92 ascertained before surgery are combined by calculation in the 3D reconstruction with an intended position 91' in the target area 90'. Here, the intended position 91' denotes a location in the data 92 ascertained before surgery relating to the region 18 of the patient's eye 14, at which the surgery object 24' should carry out a certain function. When injecting stem cells, the intended position 91 in the target area 90 corresponds to the envisaged location for the stem cell injection in the retina 15.

Methods for segmenting the tissue structures and tissue layers are applied for the purposes of determining the intended position 91' and/or the target area 90' in the data 92 ascertained before surgery. Alternatively, the intended position 91' and/or the target area 90' can also be marked by a surgeon in the data 92 ascertained before surgery.

The intended position 91' and/or the target area 90' are transferred from the computer program containing the data 92 ascertained before surgery relating to the region 18 of the patient's eye 14 to the 3D reconstruction 94 of the region 18 of the patient's eye 14 which was ascertained from the at least two data records relating to overlap regions in the form of at least partly overlapping portions of the region 18 of the patient's eye 14 and of the section 84 of the surgery object 24. Here, the registration method, which spatially relates the data 92 ascertained before surgery with the 3D reconstruction, serves for transfer purposes. As a result, the intended position 91' in the target area 90' in the data 92 ascertained before surgery is mapped onto the intended position 91 and the target area 90 of the region 18 of the patient's eye 14. Alternatively, the surgeon can also directly mark the intended position 91 and/or the target area 90 in the 3D reconstruction 94 of the region 18 of the patient's eye 14. Then, the guide variable is ascertained by processing data of the target area 90' in the data 92 ascertained before surgery or of the 3D reconstruction 94.

Figure 8:
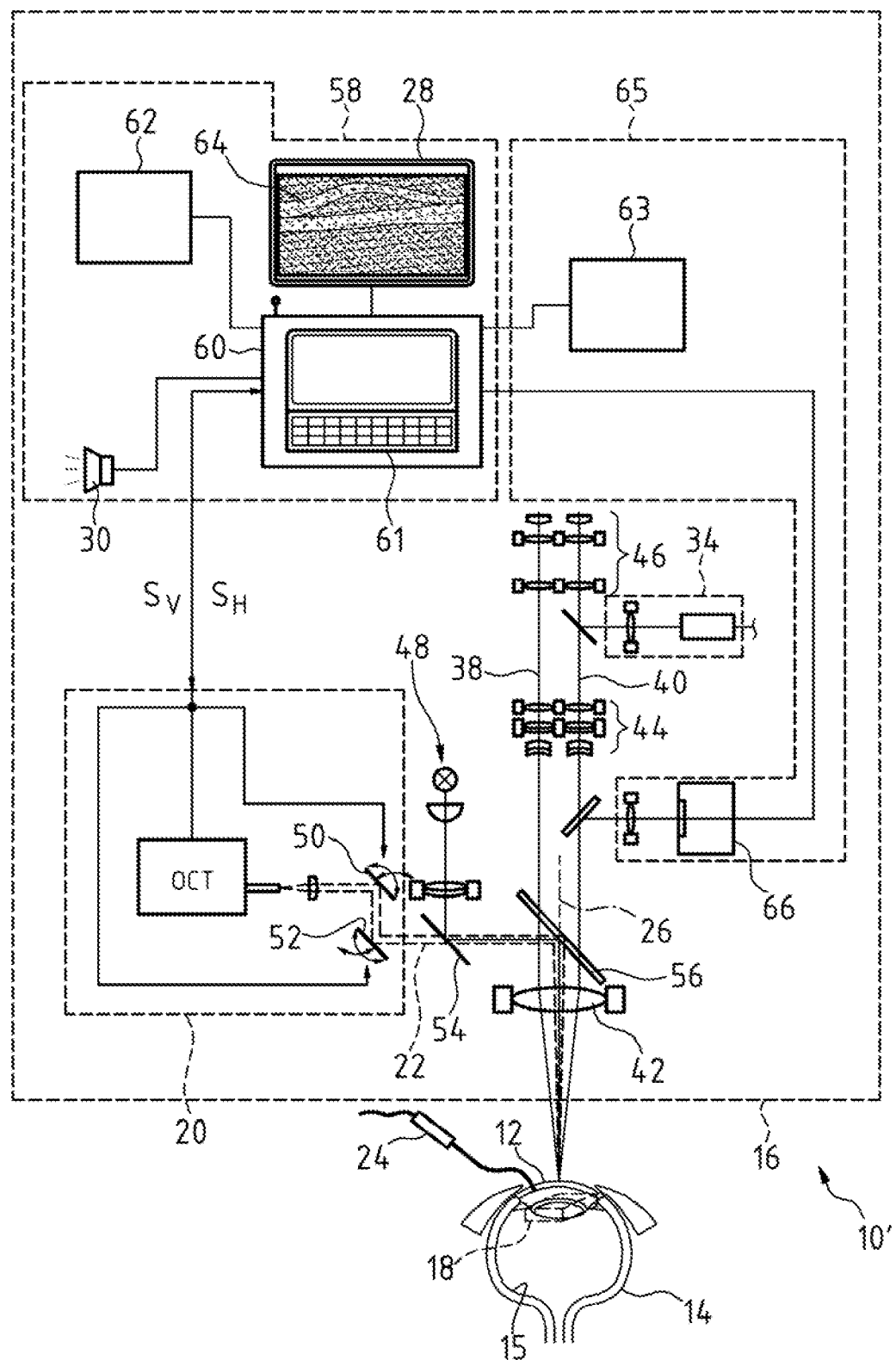
FIG. 8 shows a second eye surgery surgical system including a surgical microscope, including an OCT device for scanning a region of a patient's eye, including a surgery object in the form of a surgical instrument and including an image providing device.

FIG. 8 shows a second eye surgery surgical system 10' including a surgical microscope 16, including an OCT device 20 for scanning a region 18 of a patient's eye 14, including an object 24 in the form of a surgical instrument and including an image providing device 65. To the extent the components and elements of the second eye surgery surgical system 10' shown in FIG. 8 correspond to the components and elements of the first eye surgery surgical system 10 visible in FIG. 1, these have been identified with the same numbers as reference signs.

The image providing device 65 contains an image capturing device 66, via which images 64 of the patient's eye 14 can be captured in real time. In addition or as an alternative thereto, the image providing device 65 contains a memory 63, in which data 92 ascertained before surgery relating to the region 18 of the patient's eye 14 are provided. The images 64 of the patient's eye 14 and the data 92 ascertained before surgery are used in addition to the data obtained by scanning the region 18 of the patient's eye 14 via the OCT scanning beam 22 of the OCT device 20 in order to calculate the 3D reconstruction 94 via the registration method in order to obtain greater accuracy in the process.

Figure 9:
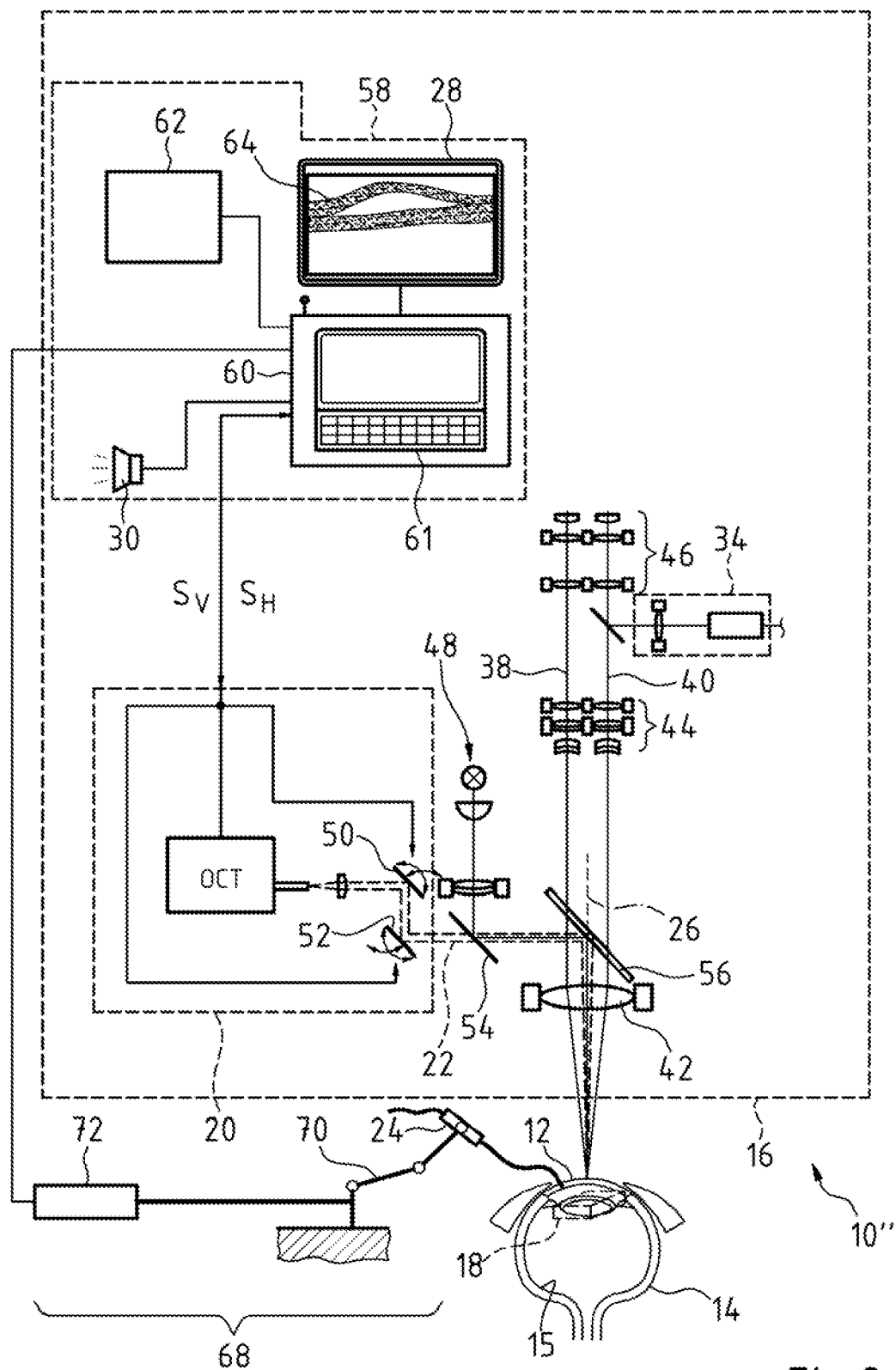
FIG. 9 shows a third eye surgery surgical system including a surgical microscope and an OCT device for scanning a region of a patient's eye, including a surgery object in the form of a surgical instrument and including a robotics unit; and, FIG. 10 shows a fourth eye surgery surgical system including a surgical microscope and an OCT device for scanning a region of a patient's eye, including a surgery object in the form of a surgical instrument, including an image providing device and including a robotics unit.

FIG. 9 shows a third eye surgery surgical system 10"' including a surgical microscope 16, including an OCT device 20 for scanning a region 18 of a patient's eye 14, including an object 24 in the form of a surgical instrument and including a robotics unit 68. To the extent the components and elements of the third eye surgery surgical system 10"' shown in FIG. 9 correspond to the components and elements of the first eye surgery surgical system 10 visible in FIG. 1 or the components and elements of the second eye surgery surgical system 10' visible in FIG. 8, these have been identified with the same numbers as reference signs.

The robotics unit 68 includes a micro robot 70 with a control unit 72. The micro robot 70 can be embodied, for example, as a manipulator for surgical instruments which has motor drives, as is provided in the ophthalmic surgical surgery system R1.1 by Preceyes B. V. To ensure automation of the operation that is as comprehensive as possible, a movement of the surgery object 24 embodied as a surgical instrument in the form of an injection needle is set in this case via the micro robot 70. The micro robot 70 of the robotics unit 68 is controlled in this case on the basis of the information items processed by the computer unit 60.

The control signals generated by the computer unit 60 for adjusting the micro robot 70 in the robotics unit 68 are guide variables for the object 24, which is embodied as a surgical instrument in the form of an injection needle, in the third eye surgery surgical system 10"'.

It should be noted that, in place of a surgery object 24 embodied as a surgical instrument in the form of an injection needle, the micro robot 70 can in principle also move a surgery object 24 in the form of a surgical instrument embodied as an applicator for a trocar or retinal pin or an implant in order hence to guide the applicator or the trocar to a target area 90 in the region 18 of the patient's eye 14. Offset information items, which specify the spatial offset of the section 84 of the surgery object 24 from a spatial intended position 91, can also be calculated to this end by the computer program on the basis of the target area 90 determined in the region 18 of the patient's eye 14 and the ascertained relative position of the surgery object 24. Then, control signals for displacing the surgery object 24 are generated from the offset information items and are transmitted to the control unit 72 of the micro robot 70.

Figure 10:
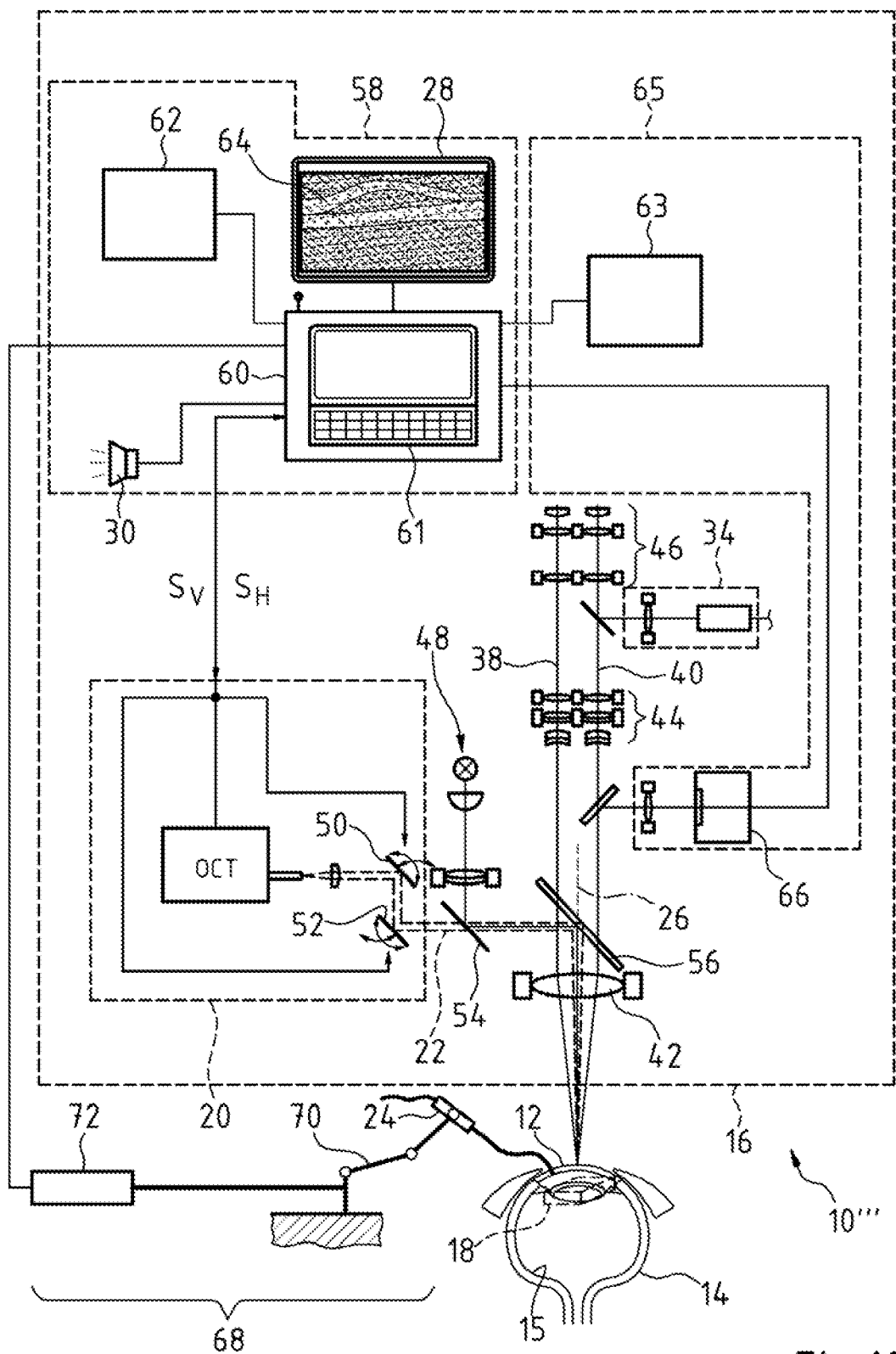

FIG. 10 shows a fourth eye surgery surgical system 10"'' including a surgical microscope 16, including an OCT device 20 for scanning a region 18 of a patient's eye, including a surgery object 24 in the form of a surgical instrument, including a robotics unit 68 and including an image providing device 65. To the extent the components and elements of the fourth eye surgery surgical system 10"'' shown in FIG. 10 correspond to the components and elements of the eye surgery surgical systems 10, 10', 10" which are visible in FIG. 1, FIG. 8 and FIG. 9 and described on the basis of these figures, these have been identified with the same numbers as reference signs. The image providing device 65 including the image capturing device 66 in this case facilitates, in turn, a calculation of the 3D reconstruction 94 of a region 18 of a patient's eye 14 with an accuracy that is greater than a 3D reconstruction 94 which is based exclusively on data from one modality, for example, scanning information obtained via an OCT device 20.

In summary, the following, in particular, should be noted: The disclosure relates to an eye surgery surgical system 10, 10', 10", 10''', including a visualization device 28 for displaying a relative position of a section 84 of a surgery object 24, 24', 24" in a 3D reconstruction 94 of a region 18 of a patient's eye 14, including at least one device for continuously providing at least two data records relating to overlap regions in the form of at least partly overlapping portions of the region 18 of the patient's eye 14 and of the section 84 of the surgery object 24, 24', 24" to a computer unit 60, including a computer program loaded in a program memory of the computer unit 60 for continuously ascertaining the relative position of the section 84 of the surgery object 24, 24', 24" and continuously ascertaining the 3D reconstruction 94 of the patient's eye 14 from the at least two data records provided, wherein the computer program contains a first program routine for continuously ascertaining the relative position of the section 84 of the surgery object 24, 24', 24" and the 3D reconstruction 94 of the region 18 of the patient's eye 14 from the at least two data records provided via a registration method and has a second program routine for adapting the registration method on the basis of a criterion.

It is understood that the foregoing description is that of the preferred embodiments of the invention and that various changes and modifications may be made thereto without departing from the spirit and scope of the invention as defined in the appended claims.

LIST OF REFERENCE SIGNS 10, 10', 10", 10''' Eye surgery surgical system
14 Patient's eye
15 Retina
16 Surgical microscope
18 Region
20 OCT device
22 OCT scanning beam
24, 24', 24" Surgery object
28 Visualization device
30 Indication signal
34 Mirroring-in data
38, 40 Stereoscopic observation beam path
42 Microscope main objective
44 Zoom system
46 Eyepiece
48 Illumination device
50, 52 Scanning mirror
54, 56 Beam splitter
58 Device
60 Computer unit
61 Input interface
62 Control member
63 Memory
64 Image
65 Image providing device
66 Image capturing device
68 Robotics unit
70 Micro robot
72 Control unit
76 Handle section
78 Marker
80 Tip
82 Opening
84 Portion
86 Capillary
88 Medium
90 Target area
90' Target area in data ascertained before surgery
91 Intended position
91' Intended position in data ascertained before surgery
92 Data ascertained before surgery
94 3D reconstruction
96 Blood vessel
98 Photoreceptors
100 Druse
102 Pupil
104 Front OCT capture region
104' Back OCT capture region
106 Front surgical microscope capture region
106' Back surgical microscope capture region
108 Camera capture region
110 Eye length
112, 112', 112", 112''' Overlap region
114 Head
116 Gonioscope capture region
118 Non-captured region

What is claimed is:

1. An eye surgery surgical system comprising:
a visualization device for displaying a relative position of a section of a surgery object in a 3D reconstruction of a region of a patient's eye;
at least one device for continuously providing at least two data records relating to overlap regions in a form of at least partly overlapping portions of the region of the patient's eye and of the section of the surgery object to a computer unit;
a computer program for continuously ascertaining the relative position of the section of the surgery object and continuously ascertaining the 3D reconstruction of the patient's eye from the at least two data records provided, wherein the computer program is stored on a non-transitory computer readable medium of the computer unit;
the computer program including a first program routine configured, when executed by a processor, to continuously ascertain the relative position of the section of the surgery object and the 3D reconstruction of the region of the patient's eye from the at least two data records provided via a registration method and including a second program routine configured to adapt the registration method on the basis of a criterion; and,
wherein the criterion is at least one characteristic of the data records from measurement accuracy of the data records, number of data records, type of data records, and type or number of different modalities of the data records;
wherein the computer program is configured to generate an actuating signal for triggering a function of at least one of the surgery object and a device of the eye surgery surgical system on the basis of at least one of the relative position of the surgery object in the 3D reconstruction of the region of the patient's eye and a type of surgery;
wherein the computer program includes:
a routine for determining at least one of a target area and an intended position for the surgery object in data ascertained before surgery;
a registration routine for registering the data ascertained before surgery with the 3D reconstruction of the region of the patient's eye; and,
a transfer routine for transferring at least one of the target area and the intended position in the data ascertained before surgery to the 3D reconstruction of the region of the patient's eye.

2. The eye surgery surgical system of claim 1, wherein the criterion takes account of properties of at least one of the data records, the region of the patient's eye, the surgery object, the eye surgery surgical system, the registration method, a currently ascertained registration, and type of surgery.

3. The eye surgery surgical system of claim 1, wherein the criterion takes account of at least one of availability of the data records, quality features of the region of the patient's eye in a form of a type or quality of the tissue or material in the region, a size of the region, a type of surgery, quality features of the surgery object in a form of dimensions or material properties thereof, quality features of devices of the eye surgery surgical system in a form of settings of the eye surgery surgical system or properties of individual components or of an illumination setting, properties of the registration method in a form of its suitability for the data records present or the speed or accuracy thereof, and a quality of a currently ascertained registration.

4. The eye surgery surgical system of claim 1 further comprising:
  a memory connected to the computer unit and configured to provide data ascertained before surgery during surgery, wherein the data ascertained before surgery originate from at least one of images of the region of the patient's eye, images or data of a target area, distances, intended positions, geometric data of the surgery object, sensor signals, and biometric patient data.

5. The eye surgery surgical system of claim 1, wherein the eye surgery surgical system is configured for a provision of the at least two data records relating to the overlap regions in the form of at least partly overlapping portions of the region of the patient's eye and of the section of the surgery object from at least one of data ascertained before surgery, images ascertained on the basis of an imaging method, sensor signals, and biometric data.

6. The eye surgery surgical system of claim 1, wherein the at least one device for the continuous provision of at least two data records is configured to recognize at least one marker arranged at the surgery object and/or in a portion of the region of the patient's eye in order hence to localize at least one of the surgery object and the portion in the 3D reconstruction of the region of the patient's eye.

7. The eye surgery surgical system of claim 6, wherein the at least one marker is uniquely assignable to the surgery object or to the portion of the region of the patient's eye.

8. The eye surgery surgical system of claim 6, wherein further information items relating to quality, structure, dimensions and/or the appearance of the surgery object or of the portion of the region of the patient's eye are stored in the eye surgery surgical system.

9. The eye surgery surgical system of claim 1, wherein the computer program is configured to adapt the registration method by virtue of at least one of a type of the registration method, parameters of the registration method, and the data records used by the registration method being altered.

10. The eye surgery surgical system of claim 1, wherein the registration method is continuously adapted during the surgery.

11. The eye surgery surgical system of claim 1, wherein the computer program includes a routine for determining a target area for the surgery object in the region of the patient's eye.

12. The eye surgery surgical system of claim 11, wherein the computer program generates a guide variable for the surgery object with respect to the target area.

13. The eye surgery surgical system of claim 12, wherein the computer program includes:

a routine for determining at least one of the target area and an intended position for the surgery object in data ascertained before surgery;
  a registration routine for registering the data ascertained before surgery with the 3D reconstruction of the region of the patient's eye; and,
  a transfer routine for transferring at least one of the target area and the intended position in the data ascertained before surgery to the 3D reconstruction of the region of the patient's eye.

14. The eye surgery surgical system of claim 1, wherein the visualization device is configured to augment data when displaying the relative position of the section of the surgery object in the 3D reconstruction of the region of the patient's eye, wherein the augmented data contain at least one of concealed regions in the 3D reconstruction, concealed regions of the surgery object, measurement values, distances, intended positions, and geometric information items in respect to the surgery object.

15. An eye surgery surgical system comprising:
  a visualization device for displaying a relative position of a section of a surgery object in a 3D reconstruction of a region of a patient's eye;
  at least one device for continuously providing at least two data records relating to overlap regions in a form of at least partly overlapping portions of the region of the patient's eye and of the section of the surgery object to a computer unit;
  a computer program for continuously ascertaining the relative position of the section of the surgery object and continuously ascertaining the 3D reconstruction of the patient's eye from the at least two data records provided, wherein the computer program is stored on a non-transitory computer readable medium of the computer unit;
  the computer program including a first program routine configured, when executed by a processor, to continuously ascertain the relative position of the section of the surgery object and the 3D reconstruction of the region of the patient's eye from the at least two data records provided via a registration method and including a second program routine configured to adapt the registration method on the basis of a criterion; and,
  wherein the criterion takes account of properties of at least one of the data records, the region of the patient's eye, the surgery object, the eye surgery surgical system, the registration method, a currently ascertained registration, and a type of surgery;
  wherein the computer program is configured to generate an actuating signal for triggering a function of at least one of the surgery object and a device of the eye surgery surgical system on the basis of at least one of the relative position of the surgery object in the 3D reconstruction of the region of the patient's eye and a type of surgery;
  wherein the computer program includes:
    a routine for determining at least one of a target area and an intended position for the surgery object in data ascertained before surgery;
    a registration routine for registering the data ascertained before surgery with the 3D reconstruction of the region of the patient's eye; and,
    a transfer routine for transferring at least one of the target area and the intended position in the data ascertained before surgery to the 3D reconstruction of the region of the patient's eye.

16. An eye surgery surgical system comprising:
- a visualization device for displaying a relative position of a section of a surgery object in a 3D reconstruction of a region of a patient's eye;
- at least one device for continuously providing at least two data records relating to overlap regions in a form of at least partly overlapping portions of the region of the patient's eye and of the section of the surgery object to a computer unit;
- a computer program for continuously ascertaining the relative position of the section of the surgery object and continuously ascertaining the 3D reconstruction of the patient's eye from the at least two data records provided, wherein the computer program is stored on a non-transitory computer readable medium of the computer unit;
- the computer program including a first program routine configured, when executed by a processor, to continuously ascertain the relative position of the section of the surgery object and the 3D reconstruction of the region of the patient's eye from the at least two data records provided via a registration method and including a second program routine configured to adapt the registration method on the basis of a criterion; and,
- wherein the criterion takes account of the availability of at least one of the data records, quality features of the region of the patient's eye in a form of a type or quality of tissue or material in the region, a size of the region, a type of surgery, quality features of the surgery object in a form of dimensions or material properties thereof, quality features of devices of the eye surgery surgical system in a form of settings of the eye surgery surgical system or properties of individual components or of an illumination setting, properties of the registration method in the form of its suitability for the data records present or the speed or accuracy thereof, and quality of a currently ascertained registration;
- wherein the computer program is configured to generate an actuating signal for triggering a function of at least one of the surgery object and a device of the eye surgery surgical system on the basis of at least one of the relative position of the surgery object in the 3D reconstruction of the region of the patient's eye and a type of surgery;
- wherein the computer program includes:
  - a routine for determining at least one of a target area and an intended position for the surgery object in data ascertained before surgery;
  - a registration routine for registering the data ascertained before surgery with the 3D reconstruction of the region of the patient's eye; and,
  - a transfer routine for transferring at least one of the target area and the intended position in the data ascertained before surgery to the 3D reconstruction of the region of the patient's eye.

17. A computer program for continuously ascertaining a relative position of a section of a surgery object and continuously ascertaining a 3D reconstruction of a region of a patient's eye from at least two data records provided, which relate to overlap regions in a form of at least partly overlapping portions of the region of the patient's eye and of the section of the surgery object, the computer program comprising:
- program code stored on a non-transitory computer readable medium, said program code being configured, when executed by a processor, to ascertain the relative position of the section of the surgery object and of the 3D reconstruction of the region of the patient's eye via a registration method which is adapted on the basis of a criterion; and,
- wherein the criterion is at least one characteristic of the data records from measurement accuracy of the data records, number of data records, type of data records, and type or number of different modalities of the data records;
- wherein the computer program is configured to generate an actuating signal for triggering a function of at least one of the surgery object and a device of the eye surgery surgical system on the basis of at least one of the relative position of the surgery object in the 3D reconstruction of the region of the patient's eye and a type of surgery;
- wherein the computer program includes:
  - a routine for determining at least one of a target area and an intended position for the surgery object in data ascertained before surgery;
  - a registration routine for registering the data ascertained before surgery with the 3D reconstruction of the region of the patient's eye; and,
  - a transfer routine for transferring at least one of the target area and the intended position in the data ascertained before surgery to the 3D reconstruction of the region of the patient's eye.

18. A computer program for continuously ascertaining a relative position of a section of a surgery object and continuously ascertaining a 3D reconstruction of a region of a patient's eye from at least two data records provided, which relate to overlap regions in the form of at least partly overlapping portions of the region of the patient's eye and of the section of the surgery object, the computer program comprising:
- program code stored on a non-transitory computer readable medium, said program code being configured, when executed by a processor, to ascertain the relative position of the section of the surgery object and of the 3D reconstruction of the region of the patient's eye via a registration method which is adapted on the basis of a criterion; and,
- wherein the criterion takes account of at least one of properties of the data records, the region of the patient's eye, the surgery object, the eye surgery surgical system, the registration method, a currently ascertained registration, and a type of surgery;
- wherein the computer program is configured to generate an actuating signal for triggering a function of at least one of the surgery object and a device of the eye surgery surgical system on the basis of at least one of the relative position of the surgery object in the 3D reconstruction of the region of the patient's eye and a type of surgery;
- wherein the computer program includes:
  - a routine for determining at least one of a target area and an intended position for the surgery object in data ascertained before surgery;
  - a registration routine for registering the data ascertained before surgery with the 3D reconstruction of the region of the patient's eye; and,
  - a transfer routine for transferring at least one of the target area and the intended position in the data ascertained before surgery to the 3D reconstruction of the region of the patient's eye.

19. A computer program for continuously ascertaining a relative position of a section of a surgery object and continuously ascertaining a 3D reconstruction of a region of a patient's eye from at least two data records provided, which relate to overlap regions in the form of at least partly overlapping portions of the region of the patient's eye and of the section of the surgery object, the computer program comprising:

program code stored on a non-transitory computer readable medium, wherein said program code is configured, when executed by a processor, to ascertain the relative position of the section of the surgery object and of the 3D reconstruction of the region of the patient's eye via a registration method which is adapted on the basis of a criterion;

wherein the criterion takes account of at least one of an availability of the data records, quality features of the region of the patient's eye in a form of a type or quality of tissue or material in the region, a size of the region, a type or surgery, quality features of the surgery object in a form of dimensions or material properties thereof, quality features of devices of the eye surgery surgical system in a form of settings of the eye surgery surgical system or properties of individual components or of an illumination setting, properties of the registration method in a form of its suitability for the data records present or the speed or accuracy thereof, and quality of the currently ascertained registration;

wherein the computer program is configured to generate an actuating signal for triggering a function of at least one of the surgery object and a device of the eye surgery surgical system on the basis of at least one of the relative position of the surgery object in the 3D reconstruction of the region of the patient's eye and a type of surgery;

wherein the computer program includes:
        a routine for determining at least one of a target area and an intended position for the surgery object in data ascertained before surgery;
        a registration routine for registering the data ascertained before surgery with the 3D reconstruction of the region of the patient's eye; and,
        a transfer routine for transferring at least one of the target area and the intended position in the data ascertained before surgery to the 3D reconstruction of the region of the patient's eye.

20. A computer-implemented method for continuously ascertaining a relative position of a section of a surgery object and continuously ascertaining a 3D reconstruction of a region of a patient's eye from at least two data records provided, which relate to overlap regions in the form of at least partly overlapping portions of the region of the patient's eye and of the section of the surgery object, via a computer program stored on a non-transitory computer readable storage medium, the computer implemented method comprising:

ascertaining the relative position of the section of the surgery object and of the 3D reconstruction of the region of the patient's eye via a registration method which is adapted on the basis of a criterion; and, wherein the criterion is one of a first criterion, a second criterion and a third criterion;

wherein the first criterion is at least one characteristic of the data records from measurement accuracy of the data records, number of data records, type of data records, and type or number of different modalities of the data records, wherein the second criterion takes account of at least one of properties of the data records, the region of the patient's eye, the surgery object, an eye surgery surgical system, the registration method, a currently ascertained registration, and a type of surgery; and, wherein the third criterion takes account of at least one of an availability of the data records, quality features of the region of the patient's eye in a form of a type or quality of tissue or material in the region, a size of the region, a type or surgery, quality features of the surgery object in a form of dimensions or material properties thereof, quality features of devices of the eye surgery surgical system in a form of settings of the eye surgery surgical system or properties of individual components or of an illumination setting, properties of the registration method in a form of its suitability for the data records present or the speed or accuracy thereof, and quality of the currently ascertained registration;

wherein the computer program is configured to generate an actuating signal for triggering a function of at least one of the surgery object and a device of the eye surgery surgical system on the basis of at least one of the relative position of the surgery object in the 3D reconstruction of the region of the patient's eye and a type of surgery;

wherein the computer program includes:
        a routine for determining at least one of a target area and an intended position for the surgery object in data ascertained before surgery;
        a registration routine for registering the data ascertained before surgery with the 3D reconstruction of the region of the patient's eye; and,
        a transfer routine for transferring at least one of the target area and the intended position in the data ascertained before surgery to the 3D reconstruction of the region of the patient's eye.

\* \* \* \* \*

UNITED STATES PATENT AND TRADEMARK OFFICE
CERTIFICATE OF CORRECTION

PATENT NO. : 12,171,499 B2  
APPLICATION NO. : 17/161536  
DATED : December 24, 2024  
INVENTOR(S) : Voigt et al.

Page 1 of 1

It is certified that error appears in the above-identified patent and that said Letters Patent is hereby corrected as shown below:

In the Specification

In Column 15:  
Line 39: delete "112", 112" with" and insert -- 112", 112''' with --

In Column 16:  
Line 25: delete "ascertain"

In Column 17:  
Line 5: delete "112''" and insert -- 112''' --

In Column 18:  
Line 31: delete "10''" and insert -- 10''' --

In Column 19:  
Line 1: delete "10', 10", 10''" and insert -- 10', 10", 10''' --  
Line 29: delete "10, 10', 10", 10''" and insert -- 10, 10', 10", 10''' --

Signed and Sealed this  
Third Day of June, 2025

Coke Morgan Stewart  
*Acting Director of the United States Patent and Trademark Office*